United States Patent
Parrish

(10) Patent No.: US 9,854,795 B2
(45) Date of Patent: *Jan. 2, 2018

(54) DRIFT REDUCTION COMPOSITIONS FOR AGRICULTURAL USE

(71) Applicant: AgQuam LLC, Spokane, WA (US)

(72) Inventor: Scott Parrish, Spokane, WA (US)

(73) Assignee: AGQUAM LLC, Spokane, WA (US)

( * ) Notice: Subject to any disclaimer, the term of this patent is extended or adjusted under 35 U.S.C. 154(b) by 335 days.

This patent is subject to a terminal disclaimer.

(21) Appl. No.: 14/462,093

(22) Filed: Aug. 18, 2014

(65) Prior Publication Data

US 2015/0045224 A1    Feb. 12, 2015

Related U.S. Application Data

(63) Continuation-in-part of application No. 13/531,333, filed on Jun. 22, 2012, now Pat. No. 8,809,234.

(60) Provisional application No. 61/500,228, filed on Jun. 23, 2011.

(51) Int. Cl.
*A01N 25/02* (2006.01)
*A01N 25/30* (2006.01)
*C05G 3/02* (2006.01)
*C05G 3/06* (2006.01)

(52) U.S. Cl.
CPC .............. *A01N 25/02* (2013.01); *A01N 25/30* (2013.01); *C05G 3/02* (2013.01); *C05G 3/06* (2013.01)

(58) Field of Classification Search
CPC .......... A01N 25/02; A01N 25/30; A01N 3/02; A01N 3/06; A01N 37/40; A01N 57/20
See application file for complete search history.

(56) References Cited

U.S. PATENT DOCUMENTS

| 6,797,673 B1 * | 9/2004 | Worthley ............... A01N 25/30 504/118 |
| 8,809,234 B1 * | 8/2014 | Parrish ................... A01N 25/02 424/1.11 |
| 2005/0026780 A1 * | 2/2005 | Parrish ................... A01N 25/10 504/119 |

* cited by examiner

*Primary Examiner* — Ali Soroush
(74) *Attorney, Agent, or Firm* — Swanson & Bratschun, L.L.C.

(57) ABSTRACT

The present disclosure relates generally to the field of agricultural chemicals and, more particularly, to compositions which can be added to agricultural chemicals for the purpose of improving efficacy and reducing drift of sprayed chemicals away from target areas. Further disclosed are processes for preparing combination water conditioning adjuvant and drift reduction compositions as well as methods of drift reduction utilizing such compositions.

74 Claims, 2 Drawing Sheets

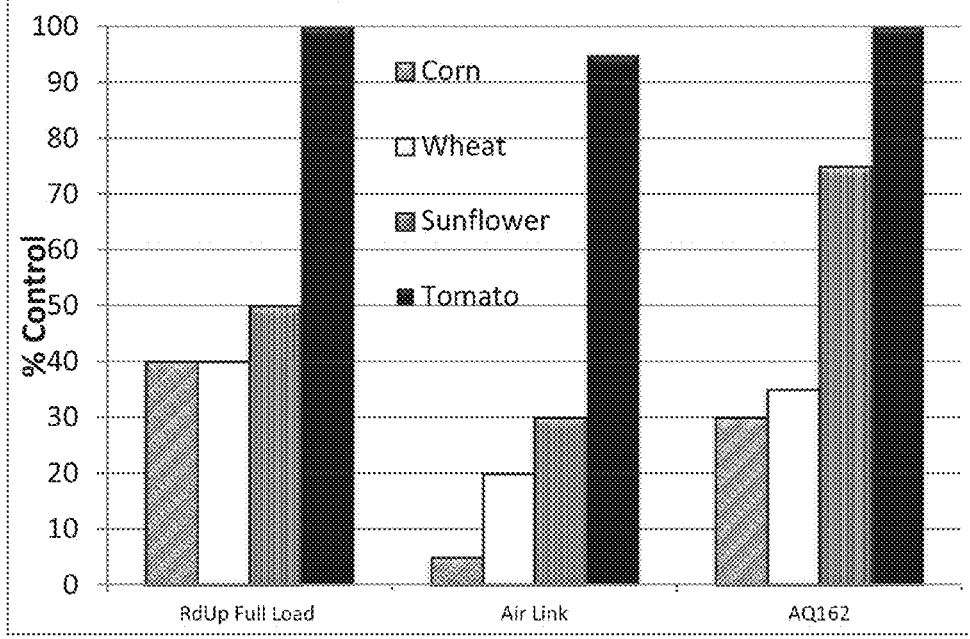

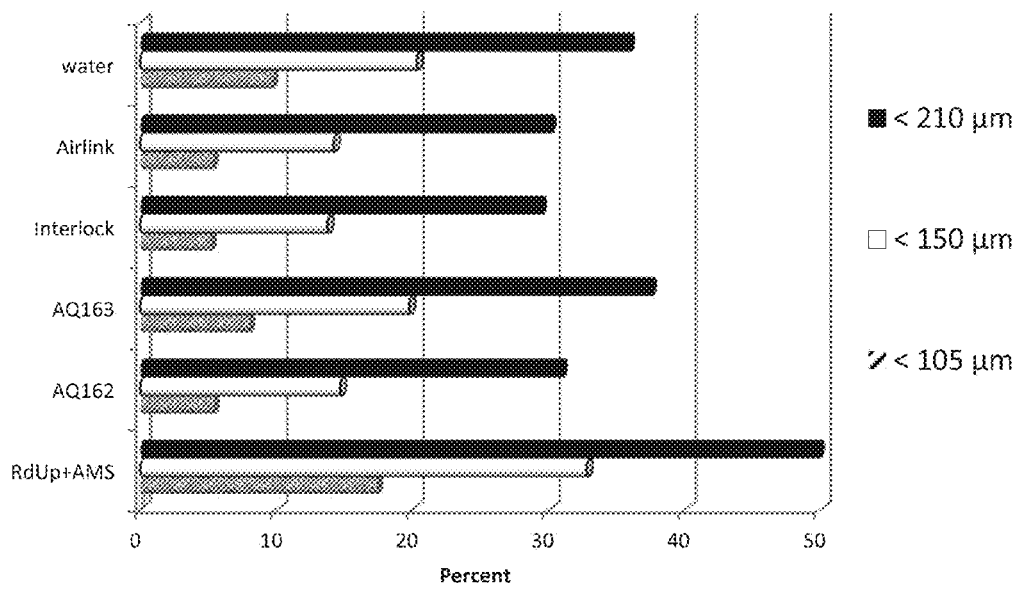

DRIFT REDUCTION COMPOSITIONS FOR AGRICULTURAL USE

CROSS-REFERENCE TO RELATED APPLICATIONS

This application is a continuation-in-part application of U.S. application Ser. No. 13/531,333, filed on Jun. 22, 2012, which will issue as U.S. Pat. No. 8,809,234 on Aug. 19, 2014, entitled "Drift Reduction Compositions for Agricultural Use" which claims priority under 35 U.S.C. §119(e) to U.S. Provisional Application Ser. No. 61/500,228, which was filed on Jun. 23, 2011, the disclosure of which is incorporated herein in its entirety.

FIELD OF THE INVENTION

The present application relates to compositions for application to agricultural land. Specifically, the present application relates to combination water conditioning adjuvant and drift reduction compositions which can be added to agricultural chemicals, such as herbicides to be sprayed on crops, for the purpose of improving efficacy and reducing drift of the sprayed chemicals away from the target areas.

BACKGROUND

Herbicide spray drift is the movement of herbicides from the target area to areas where herbicide application was not intended. Herbicide spray drift may injure susceptible crops and could cause prohibited residues in the harvested crops. Drift can cause non-uniform application in a field with possible crop damage and/or poor weed control. Drift can also cause surface water contamination and health risks for animals and people. Spray drift can be reduced by increasing droplet size of the spray, as wind moves larger droplets less than smaller droplets.

Hard water, when used as a carrier for spray solutions, can adversely affect the effectiveness of certain salt-formulated herbicides such as glyphosate, sethoxydim, imazethapyr, glufosinate, 2,4-D amine salt and dicamba. Natural waters usually contain ions of calcium ($Ca^{+2}$), magnesium ($Mg^{+2}$), and iron ($Fe^{+3}$). Hard water ions can bind with salts of certain herbicides and with some surfactants to form insoluble salts and reduce the effectiveness of herbicides and surfactants.

Adding agents such as ammonium sulfate (AMS), has been shown to increase herbicide efficacy on a broad spectrum of weed species under hard water conditions. U.S. Pat. No. 4,681,617 to Ghyczy et al. entitled "Phospholipid Compositions and their Use in Plant Protection Spray Mixtures" discloses the use of phospholipids as drift reduction agents.

U.S. Pat. No. 6,797,673 to Worthley et al. entitled "Lecithin-Containing Drift Control Composition for Use in Spraying Agricultural Acreage" discloses the use of lecithin as drift reduction agent in a composition comprising a methyl ester and a non-ionic surfactant.

SUMMARY

The present disclosure provides combination water conditioning adjuvant and drift reduction compositions for agricultural use. Included are compositions comprising a water conditioning adjuvant comprising a concentrated mineral acid and an amine surfactant and a drift reduction agent.

Also disclosed are processes for preparing a combination water conditioning adjuvant and drift reduction composition for agricultural use comprising adding a concentrated mineral acid to an amine surfactant to obtain a water conditioning adjuvant and adding the water conditioning adjuvant to a drift reduction agent.

Further disclosed are methods for reducing drift during release of agricultural chemicals comprising a combination water conditioning adjuvant and drift reduction composition comprising forming an aqueous composition suitable for treating agricultural acreage by mixing a combination water conditioning adjuvant and drift reduction composition for agricultural use, carrier water and a bioactive material and spraying the aqueous composition on agricultural acreage.

BRIEF DESCRIPTION OF THE DRAWINGS

FIG. 1 illustrates the relative control of 4 indicator plant species using ROUNDUP in combination with one of FULL LOAD (a water conditioning adjuvant), AIR LINK (commercial standard drift reduction agent) and AQ 162 (combination water conditioning adjuvant and drift reduction composition).

FIG. 2 illustrates spray droplet size comparing two combination water conditioning adjuvant and drift reduction compositions, AQ 163 and AQ 162 at a concentration of 0.25% v/v, to commercial drift reduction standards AIR LINK and INTERLOCK at the same concentration.

DETAILED DESCRIPTION

Reference will now be made in detail to representative embodiments of the invention. While the invention will be described in conjunction with the enumerated embodiments, it will be understood that the invention is not intended to be limited to those embodiments. On the contrary, the invention is intended to cover all alternatives, modifications, and equivalents that may be included within the scope of the present invention as defined by the claims.

One skilled in the art will recognize many methods and compositions similar or equivalent to those described herein, which could be used in and are within the scope of the practice of the present invention. The present invention is in no way limited to the methods and compositions described.

Unless defined otherwise, technical and scientific terms used herein have the same meaning as commonly understood by one of ordinary skill in the art(s) to which this invention belongs. Although any methods, processes, and compositions similar or equivalent to those described herein can be used in the practice or testing of the invention, the preferred methods, processes and compositions are now described.

All publications, published patent documents, and patent applications cited in this disclosure are indicative of the level of skill in the art(s) to which the disclosure pertains. All publications, published patent documents, and patent applications cited herein are hereby incorporated by reference to the same extent as though each individual publication, published patent document, or patent application was specifically and individually indicated as being incorporated by reference.

As used in this disclosure, including the appended claims, the singular forms "a," "an," and "the" include plural references, unless the content clearly dictates otherwise, and are used interchangeably with "at least one" and "one or more."

As used herein, the term "about" represents an insignificant modification or variation of the numerical value such that the basic function of the item to which the numerical value relates is unchanged.

As used herein, the term "use in agriculture" or "agricultural use" means use of methods, processes or compositions in the cultivation of plants.

As used herein, the term "adjuvant" means a composition which increases the efficacy of a bioactive material, including but not limited to increasing the efficacy of a herbicide.

As used herein, the term "bioactive material" means agricultural chemicals, including but not limited to pesticides, herbicides, fungicides, insecticides, acaricides, nematocides, foliar nutrients, defoliants, plant growth regulators, and molluscicides.

As used herein, the term "carrier water" means water used to dilute agricultural chemicals, including but not limited to spray application of such chemicals.

As used herein, the term "drift" or "spray drift" means the movement of a bioactive material from the target area to areas where application of the bioactive material was not intended.

As used herein, the term "drift reduction agent" or "drift reduction composition" means a composition which can reduce drift or spray drift, by means including but not limited to increasing the droplet size of a sprayed liquid. The drift reduction agent or drift reduction composition includes but is not limited to phospholipids (e.g. lecithin), vegetable colloids, non-derivatized guar gum, non-cationic derivatized guar gum, cationic guar gum, polyethylene oxides, poly (vinyl pyrrolidones), polyacrylamides, a non-ionic emulsifier, a cationic emulsifier and an anionic emulsifier.

As used herein, the term "lecithin" means a composition comprising one or more types of phospholipids, including but not limited to phosphatidylcholine, phosphatidylethanolamine, phosphatidylserine, and phosphatidylinositol. Lecithin may further comprise compositions, including but not limited to triglycerides, fatty acids, glycolipids and carbohydrates. Lecithin may be derived from sources including but not limited to soy, safflower, sunflower, and rapeseed.

As used herein, the term "mineral acid" means an acid, optionally a concentrated mineral acid, which does not comprise any carbon atoms, including but not limited to sulfuric acid, perchloric acid, hydroiodic acid, hydrobromic acid, hydrochloric acid, and nitric acid. As used herein, the term "mineral acid" does not include phosphoric acid. As used herein, the term "concentrated mineral acid" includes but is not limited to sulfuric acid more than 90% concentrated, perchloric acid that is more than 50% concentrated, hydroiodic acid which is more than 40% concentrated, hydrobromic acid which is more than 50% concentrated, hydrochloric acid which is more than 25% concentrated, and nitric acid which is more than 60% concentrated.

As used herein, the term "amine surfactant" means a surfactant comprising an amine group, including but not limited to octyl amine, lauryl amine, stearyl amine, oleyl amine, tallow amine, cetylamine, N-tetradecyl amine, cocoamine, hydrogenated tallow amine, di(hydrogenated) tallow amine, dicocoalkyl amine, N-tridecyltridecanamine, N-methylstearylamine, distearyl amine, ether amine and dialkyl($C_8$-$C_{20}$)amine. Amine surfactants include cationic surfactants such as alkyl dimethylamines, alkyl amidopropylamines, alkyl imidazoline derivatives, quaternised amine ethoxylates, and quaternary ammonium compounds or non-ionic surfactants such as amine oxides, ether amine derivatives, ethoxylated alkanolamides, fatty acid alkanolamides. In one embodiment, the amine surfactant is tallow amine. In one aspect, the ether amine is selected from alkoxylated tertiary ether amine, alkoxylated and non-alkoxylated quaternary etheramine, and alkoxylated etheramine oxide. As used herein, the term "non-ionic surfactant" means a surfactant which does not have a positive or negative charge, including but not limited to alkyl polyoxyethylene ether, polyoxypropylene glycol, an alkyl phenol ethoxylate, an alcohol ethoxylate, a sugar ether, a glucoside alkyl ether, a sucrose ester, a sorbitan ester ethoxylate, a crop oil concentrate, morpholine amide and a block copolymer.

As used herein, the term "cationic emulsifier" means an emulsifier which has a positive charge, including but not limited to primary, secondary and tertiary amines and salts thereof, alkyltrimethylammonium salts, dialkyldimethylammonium salts, trialkylmethylammonium salts, tetraalkylammonium salts, alkoxylated alkylammonium salts, ester quats, diamidoamine quats, alkyloxyalkyl quats, quaternary alkylphosphonium salts, tertiary alkylsulfonium salts, alkylimidazolium salts, alkyloxazolinium salts, alkylpyridium salts and N,N-dialkylmorpholinium salts; the cationic emulsifier may comprise chloride, bromide, methyl sulfate, sulfate or the like as counterion.

As used herein, the term "anionic emulsifier" means an emulsifier which has a negative charge, including but not limited to alkyl sulfates, arylsulfonates, fatty alcohol sulfates, alkylsulfonates, paraffinsulfonates, alkyl ether sulfates, alkyl polyglycol ether sulfates, fatty alcohol ether sulfates, alkylbenzenesulfonates (e.g. dodecylbenzene sulfonate), alkylnaphthylsulfonates, alkylphenyl ether sulfates, alkyl phosphates, phosphoric acid mono-, di-, and tri-esters, alkyl ether phosphates, ethoxylated fatty alcohol phosphoric esters, alkylphenyl ether phosphates, phosphonic esters, sulfosuccinic diesters, sulfosuccinic monoesters, ethoxylated sulfosuccinic monoesters, ulfosuccinamides, a-olefinsulfonates, alkyl carboxylates, alkyl ether carboxylates, alkyl polyglycol carboxylates, fatty acid isethionate, fatty acid methyltauride, fatty acid sarcoside, arylsulfonates, naphthalenesulfonates, alkyl glyceryl ether sulfonates, sulfated oils, polyacrylates and/or a-sulfa fatty acid esters. The anionic emulsifier may comprise, for example, sodium, potassium, ammonium, monoethanolammonium, triethanolammonium or other organically substituted ammonium cations as counterion.

As used herein, the term "non-ionic emulsifier" means an emulsifier which does not have a positive or negative charge, including but not limited to alcohols, alcohol ethoxylates, polyoxyethylene-polyoxypropylene-alkyl ethers, amine alkoxylates, fatty alcohol polyglycol ethers, fatty amine polyglycol ethers, fatty acid ethoxylates, fatty acid polyglycol esters, glyceride monoalkoxylates, alkanolamides, fatty acid alkanolamides, ethoxylated alkanolamides, ethoxylated esters, fatty acid alkylolamido ethoxylates, ethylene oxide-propylene oxide block copolymers, alkylphenol ethoxylates, alkyl glucosides, partial esters of aliphatic carboxylic acids with polyfunctional alcohols, polyethoxylated polystyrene phenyl ethers, amides of aliphatic carboxylic acids with alkanolamines, ethoxylated amides of aliphatic carboxylic acids with alkanolamines, morpholine amide and polyalkoxylated organopoly-siloxanes.

As used herein, the term "surfactant" means any compound that lowers the surface tension of a liquid, the interfacial tension between two liquids or the tension between a liquid and a solid.

As used herein, the term "water conditioning" means the property of increasing the solubility of a bioactive material, e.g. an herbicide, in water and/or binding to ions in water, including but not limited to cations in hard water.

Applicant herein discloses combination water conditioning adjuvant and drift reduction compositions which reduce the problem of spray drift by providing at least one component that increases droplet size and at least one adjuvant component which improves the efficacy of agricultural spray solutions under hard water conditions.

Generally, when a farmer desires to spray a bioactive material, including but not limited to a post-emergence herbicide such as glyphosate, under hard water conditions, the farmer needs to add a water conditioning adjuvant which binds to the ions in hard water. If no water conditioning adjuvant is added, then the ions in hard water tend to bind to the bioactive material substantially reducing efficacy. The most common water conditioning adjuvant used is ammonium sulfate (AMS). Approximately 17 pounds of dry AMS are added and mixed for each 100 gallons of carrier water used for spraying bioactive materials. AMS is bulky and inconvenient for a farmer to use. Applicant has disclosed in U.S. Patent Application Publication No. 2005/0026780, which is incorporated herein in its entirety, that a mineral acid, for example sulfuric acid, can be formulated as a water conditioning adjuvant when combined with an amine surfactant, such as tallow amine, providing water conditioning adjuvant properties which are equal to or superior to AMS.

Additionally, when a farmer desires to spray a bioactive material, the farmer generally needs to reduce the drift of the bioactive material outside of the target area of application. Among the most commonly used drift reduction agents is lecithin (e.g. soy lecithin) which serves to increase the droplet size of the sprayed bioactive material. Drift reduction agents used by farmers include phospholipids, vegetable colloids, non-derivatized guar gum, non-cationic derivatized guar gum, cationic guar gum, polyethylene oxides, poly(vinyl pyrrolidones), polyacrylamides, a non-ionic emulsifier, a cationic emulsifier and an anionic emulsifier. Generally, the drift reduction agent is a separate composition, carried in a container separate from the water conditioning adjuvant that a farmer must add to carrier water in addition to the water conditioning adjuvant.

Applicant has developed a composition and process of making said composition which combines a water conditioning adjuvant with a drift reduction agent into one combination composition contained in a single container. The combination water conditioning adjuvant and drift reduction composition provides a high level of convenience to the farmer such that the single combined composition provides the benefits of both water conditioning adjuvant and drift reduction. Further, the combination water conditioning adjuvant and drift reduction composition disclosed herein provides water conditioning adjuvant properties and drift reduction as effective as or superior to commercial standards.

A concentrated mineral acid, such as sulfuric acid, can react adversely with organic compounds, such as phospholipids, forming undesirable by-products, see Example 1. Applicant has surprisingly shown that a concentrated mineral acid, such as sulfuric acid, can be maintained in combination with organic drift reduction compounds, such as phospholipids, without reactions resulting in undesirable by-products, if an amine surfactant is used to stabilize the combination, see Example 1. This surprising result has been achieved, in one embodiment, by providing for the amine surfactant tallow amine in equal or greater concentration than the concentration of the sulfuric acid before the addition of phospholipids (e.g. lecithin). This result is particularly surprising because in the presence of some amine compounds which are not surfactants (e.g. urea), a concentrated mineral acid (e.g. sulfuric acid) reacts adversely with an organic drift reduction compound (e.g. lecithin) resulting in a cloudy suspension and separation of liquid components, see Example 1.

Applicant has further found that the introduction of excessive water into the combination water conditioning adjuvant and drift reduction composition results in adverse reaction between the mineral acid and the drift reduction agent. One means by which water is minimized in one embodiment of the combination water conditioning and drift reduction composition disclosed herein is by use of concentrated mineral acid which itself has a low water content.

Applicant has also found that when the combination water conditioning adjuvant and drift reduction composition is introduced into carrier water, e.g. 100 gallon tank, for agricultural spray application, the mineral acid does not adversely react with the drift reduction agent due to the large scale of dilution.

In one embodiment, a composition for agricultural use is disclosed comprising a water conditioning adjuvant comprising a concentrated mineral acid and an amine surfactant; and a drift reduction agent selected from the group consisting of at least one phospholipid, vegetable colloids, non-derivatized guar gum, non-cationic derivatized guar gum, cationic guar gum, polyethylene oxides, poly(vinyl pyrrolidones), polyacrylamides, a non-ionic emulsifier, a cationic emulsifier which is not an amine surfactant, and an anionic emulsifier. In some embodiments, the drift reduction agent is at least one phospholipid selected from the group consisting of lecithin, phosphatidic acid, phosphotidyl ethanolamine, phosphatidylcholine, phosphatidylserine, phosphatidylinositol, phosphatidylinositol phosphate, phosphatidylinositol biphosphate, phosphatidylinositol triphosphate, and mixtures thereof. In some embodiments, the concentrated mineral acid can be selected from the group consisting of sulfuric acid, perchloric acid, hydroiodic acid, hydrobromic acid, hydrochloric acid, and nitric acid. In some embodiments, the amine surfactant can be selected from the group consisting of octyl amine, lauryl amine, stearyl amine, oleyl amine, tallow amine, cetylamine, N-tetradecyl amine, cocoamine, hydrogenated tallow amine, di(hydrogenated) tallow amine, dicocoalkyl amine, N-tridecyltridecanamine, N-methylstearylamine, distearyl amine, ether amine and dialkyl($C_8$-$C_{20}$)amine. In one aspect, the concentration of tallow amine can be equal to or greater than the concentration of sulfuric acid in the composition. Embodiments include the composition further comprising an oil selected from the group consisting of free fatty acids, mineral oil, vegetable oil, methylated seed oil, ethylated seed oil, butylated seed oil, and mixtures thereof. Embodiments include the composition comprising an oil selected from soybean oil, sunflower oil, cotton seed oil, crop oil concentrate and methylated soybean oil. Embodiments further include the composition comprising a glycol selected from the group consisting of diethylene glycol, triethylene glycol, tetraethylene glycol and pentaethylene glycol. Embodiments also include the composition comprising a non-ionic surfactant selected from the group consisting of an alkyl polyoxyethylene ether, polyoxypropylene glycol, an alkyl phenol ethoxylate, an alcohol ethoxylate, a sugar ether, a glucoside alkyl ether, a sucrose ester, a sorbitan ester ethoxylate, a crop oil concentrate, morpholine amide and a block copolymer. In one aspect, the sugar ether is selected from the group consisting of glucoside alkyl ether, xylose alkyl ether, arabinose alkyl ether, mannose alkyl ether, ribose alkyl ether, rhamnose alkyl ether, galactose alkyl ether, sucrose alkyl ether, maltose alkyl ether, lactose alkyl ether, fructose alkyl ether, and raffinose alkyl ether. In one aspect, the alkyl group has 8 to 20 carbon atoms. In another aspect, the alky group has 10 to 18 carbon atoms. In one aspect, the surfactant is Isoclear® 55. In one aspect, the composition does not contain and is not contacted with ammonium sulfate (AMS). Embodiments include the composition comprising an emulsifier and/or an additive selected from a buffering agent, a defoaming agent, a wetting agent, a sticking agent and a tank cleaner. In one aspect, the water content of the composition is below 5% (v/v), before dilution of the composition in carrier water. In another aspect, the water content of the composition is below 1% (v/v), before dilution of the composition in carrier water. Embodiments of the invention include a composition comprising 1-25% by weight or volume concentrated mineral acid, 10-50% by weight or volume amine surfactant, 10-60% by weight or volume phospholipid, 10-50% by weight or volume oil and 5-50% by weight or volume glycol. Embodiments of the invention further include a composition comprising 1-25% by weight or volume concentrated sulfuric acid, 10-50% by weight or volume tallow amine, 10-60% by weight or volume lecithin, 10-50% by weight or volume methylated seed oil and 5-50% by weight or volume diethylene glycol.

In one aspect, the fatty acid is selected from the group consisting of free C12-C18 fatty acid, CAS No. 67762-38-3 (Fatty acids, C16-18 and C18-unsatd., Me esters), CAS No. 162627-18-1 (Fatty acids, C18-unsatd., trimers, reaction products with triethylenetetramine), polyethylene sorbitol C8-C18 fatty acid esters, CAS No. 68553-02-6 (fatty acids, coco, esters with polyethylene glycol ether with glycerol (3:1)), CAS No. 68424-50-0 (fatty acids, tall-oil, C12-15-alkyl esters, sulfated, sodium salts), and CAS No. 61790-90-7 (fatty acids, tall-oil, hexaesters with sorbitol, ethoxylated). In another aspect, the fatty acid is CAS No. 67701-08-0 (fatty acid, C16-C18 and C18-unsatd).

The present application also discloses a process of preparing a composition for agricultural use comprising adding a concentrated mineral acid to an amine surfactant to obtain a water conditioning adjuvant; and adding the water conditioning adjuvant to a drift reduction agent selected from the group consisting of at least one phospholipid, vegetable colloids, non-derivatized guar gum, non-cationic derivatized guar gum, cationic guar gum, polyethylene oxides, poly (vinyl pyrrolidones), polyacrylamides, a non-ionic emulsifier, a cationic emulsifier which is not an amine surfactant, and an anionic emulsifier. In some embodiments, the process comprises a drift reduction agent that is at least one phospholipid selected from the group consisting of lecithin, phosphatidic acid, phosphotidyl ethanolamine, phosphatidylcholine, phosphatidylserine, phosphatidylinositol, phosphatidylinositol phosphate, phosphatidylinositol biphosphate, phosphatidylinositol triphosphate, and mixtures thereof. In some embodiments, the concentrated mineral acid of the process can be selected from the group consisting of sulfuric acid, perchloric acid, hydroiodic acid, hydrobromic acid, hydrochloric acid, and nitric acid. Embodiments of the process include an amine surfactant selected from the group consisting of octyl amine, lauryl amine, stearyl amine, oleyl amine, tallow amine, cetylamine, N-tetradecyl amine, cocoamine, hydrogenated tallow amine, di(hydrogenated) tallow amine, dicocoalkyl amine, N-tridecyltridecanamine, N-methylstearylamine, distearyl amine, ether amine and dialkyl($C_8$-$C_{20}$)amine. In one aspect, the concentration of tallow amine used in the process can be equal to or greater than the concentration of sulfuric acid in the composition. In some embodiments, the process comprises addition of an oil selected from the group consisting of free fatty acids, mineral oil, vegetable oil, methylated seed oil, ethylated seed oil, butylated seed oil, and mixtures thereof. Embodiments of the process include addition of an oil selected from soybean oil, sunflower oil, cotton seed oil, crop oil concentrate and methylated soybean oil. In some embodiments, the process comprises addition of a glycol selected from the group consisting of diethylene glycol, triethylene glycol, tetraethylene glycol and pentaethylene glycol. Embodiments of the process also include addition of a non-ionic surfactant selected from the group consisting of an alkyl polyoxyethylene ether, polyoxypropylene glycol, an alkyl phenol ethoxylate, an alcohol ethoxylate, a sugar ether, a glucoside alkyl ether, a sucrose ester, a sorbitan ester ethoxylate, a crop oil concentrate, morpholine amide and a block copolymer. In one aspect, the process does not add ammonium sulfate (AMS) to the composition or contact the composition with AMS. Some embodiments of the process comprise adding an emulsifier and/or an additive selected from a buffering agent, a defoaming agent, a wetting agent, a sticking agent and a tank cleaner. In one embodiment of the process, the water content of the composition is below 5% (v/v), before dilution of the composition in carrier water. Embodiment of the process include, the water content of the composition is below 1% (v/v), before dilution of the composition in carrier water.

The present application further discloses a product resulting from a specified process wherein a composition is prepared by a process comprising adding a concentrated mineral acid to an amine surfactant to obtain a water conditioning adjuvant; and adding the water conditioning adjuvant to a drift reduction agent selected from the group consisting of at least one phospholipid, vegetable colloids, non-derivatized guar gum, non-cationic derivatized guar gum, cationic guar gum, polyethylene oxides, poly(vinyl pyrrolidones), polyacrylamides, a non-ionic emulsifier, a cationic emulsifier which is not an amine surfactant, and an anionic emulsifier. In some embodiments of the product, the process comprises a drift reduction agent selected to be at least one phospholipid selected from the group consisting of lecithin, phosphatidic acid, phosphotidyl ethanolamine, phosphatidylcholine, phosphatidylserine, phosphatidylinositol, phosphatidylinositol phosphate, phosphatidylinositol biphosphate, phosphatidylinositol triphosphate, and mixtures thereof. In some embodiments of the product, the process comprises concentrated mineral acid selected from the group consisting of sulfuric acid, perchloric acid, hydroiodic acid, hydrobromic acid, hydrochloric acid, and nitric acid. In some embodiments of the product, the process comprises amine surfactant selected from the group consisting of octyl amine, lauryl amine, stearyl amine, oleyl amine, tallow amine, cetylamine, N-tetradecyl amine, cocoamine, hydrogenated tallow amine, di(hydrogenated) tallow amine, dicocoalkyl amine, N-tridecyltridecanamine, N-methylstearylamine, distearyl amine, ether amine and dialkyl($C_8$-$C_{20}$)amine. In one aspect, the concentration of tallow amine can be equal to or greater than the concentration of sulfuric acid in the composition. Embodiments of the product result from a process comprising addition of an oil selected from the group consisting of free fatty acids, mineral oil, vegetable oil, methylated seed oil, ethylated seed oil, butylated seed oil, and mixtures thereof. Some embodiments of the product result from a process which comprises addition of an oil selected from soybean oil, sunflower oil, cotton seed oil, crop oil concentrate and methylated soybean oil. Embodiments of the product further include the result of a process comprising addition of a glycol selected from the group consisting of diethylene glycol, triethylene glycol, tetraethylene glycol and pentaethylene glycol. Embodiments of the product also include the result of a process comprising addition of a non-ionic surfactant selected from the group consisting of an alkyl polyoxyethylene ether, polyoxypropylene glycol, an alkyl phenol ethoxylate, an alcohol ethoxylate, a sugar ether, a glucoside alkyl ether, a sucrose ester, a sorbitan ester ethoxylate, a crop oil concentrate, morpholine amide and a block copolymer. In one aspect, the composition does not contain and is not contacted with ammonium sulfate (AMS). Embodiments of the product include the results of a process comprising addition of an emulsifier and/or an additive selected from a buffering agent, a defoaming agent, a wetting agent, a sticking agent and a tank cleaner. In one aspect, the water content of the composition is below 5% (v/v), before dilution of the composition in carrier water. In another aspect, the water content of the composition is below 1% (v/v), before dilution of the composition in carrier water.

The present application also discloses a method for reducing drift during release of an aqueous composition suitable for treating agricultural acreage comprising the steps of: forming the aqueous composition suitable for treating agricultural acreage by mixing a composition for agricultural use (comprising a water conditioning adjuvant comprising a concentrated mineral acid and an amine surfactant; and a drift reduction agent selected from the group consisting of at least one phospholipid, vegetable colloids, non-derivatized guar gum, non-cationic derivatized guar gum, cationic guar gum, polyethylene oxides, poly(vinyl pyrrolidones), polyacrylamides, a non-ionic emulsifier, a cationic emulsifier which is not an amine surfactant, and an anionic emulsifier), carrier water and a bioactive material; and spraying the aqueous composition on agricultural acreage; wherein the composition is about 0.25% (v/v) to about 5% (v/v) of the aqueous composition. Embodiments of the method for reducing spray drift include selection of the bioactive material from the group consisting of pesticides, herbicides, fungicides, insecticides, acaricides, nematocides, foliar nutrients, defoliants, plant growth regulators, and molluscicides. Embodiments of the method for reducing spray drift also include selection of the bioactive material from the group consisting of glyphosate (N-(phosphonomethyl)glycine) and dicamba.

In one embodiment, the mineral acid is sulfuric acid, including but not limited to concentrated sulfuric acid which is at least 93% concentrated sulfuric acid. In another embodiment, the sulfuric acid is at least 98% concentrated sulfuric acid. In other embodiments, mineral acids such as concentrated perchloric acid, hydroiodic acid, hydrobromic acid, hydrochloric acid, and nitric acid can be used. The mineral acid may be used in amounts of between about 1% and about 50% (weight:weight or volume:volume) in the water conditioning adjuvant composition. In some embodiments the amount is between about 1% and about 25%. In other embodiments, the amount of mineral acid may be about 1%, about 2%, about 3%, about 4%, about 5%, about 6%, about 7%, about 8%, about 9%, about 10%, about 12%, about 13%, about 14%, about 15%, about 16%, about 17%, about 18%, about 19%, about 20%, about 21%, about 22%, about 23%, about 24%, or about 25% of the water conditioning adjuvant composition.

An amine surfactant may be used in amounts of between about 10% and about 50% (weight:weight or volume:volume) in the water conditioning adjuvant composition and/or the drift reduction composition. In some embodiments, the amount of amine surfactant may be about 20%, about 22%, about 24%, about 26%, about 28%, about 30%, about 32%, about 34%, about 36%, about 38%, about 40%, about 42%, about 44%, about 46%, about 48%, or about 50% (weight:weight or volume:volume) of the water conditioning adjuvant composition, drift reduction composition, or combination composition comprising both water conditioning adjuvant and drift reduction agent. In some embodiments, the amount of amine surfactant is less than or equal to 20%, is less than or equal to 22%, is less than or equal to 24%, is less than or equal to 26%, is less than or equal to 28%, is less than or equal to 30%, is less than or equal to 32%, is less than or equal to 34%, is less than or equal to 36%, is less than or equal to 38%, is less than or equal to 40%, is less than or equal to 42%, is less than or equal to 44%, is less than or equal to 46%, is less than or equal to 48%, or is less than or equal to 50% (weight:weight or volume:volume) of the water conditioning adjuvant composition, drift reduction composition, or combination composition comprising both water conditioning adjuvant and drift reduction agent. In one embodiment, the amount of amine surfactant is greater than or equal to the amount of mineral acid (weight:weight or volume:volume).

The water conditioning adjuvant composition and/or the drift reduction agent optionally comprise an emulsifier which may serve to prevent separation of tallow amine from the mixture or otherwise improve the effectiveness or usability of the composition.

The water conditioning adjuvant composition optionally further comprises a glycol. Such glycols include diethylene glycol (DEG), triethylene glycol, tetraethylene glycol and pentaethylene glycol. Glycol can be added in an amount of between 5% and about 50% and up. Glycol can be added to the compositions in divided amounts, for example, about 5% to about 50% added prior to the addition of the mineral acid and/or the amine surfactant, followed by the remainder of the glycol. Among other benefits, glycol provides flowability to the composition.

Exemplary drift reduction agents comprising phospholipids include commercially available lecithin-containing drift reduction agents such as SOLEC 3F-UB, LIBERATE, LI 700, AIRLINK, ACTIFY, COMPADRE, FIRST CHOICE ALPHA APS, FRANCHISE, MONTEREY SUPER 7, MSO CONCENTRATE WITH LECI-TECH, PHT AD-BUFF, POLYTEX L525, PROLEC, SYNTHEX GL, TORPEDO, TRANSMIT, 3F-UB; TURFGO PROFESSIONAL TURF PRODUCTS LI 700, VADER, WEATHER GARD COMPLETE, AF 1; AF 1 (lecithin); ACTI-FLOW 68SB; ADLEC; ALCOLEC BS; ALCOLEC F 100; ALCOLEC PC 75; ALCOLEC PG; ALCOLEC S; ALCOLEC Z 7; BASIS LP 2070R; BASIS LP20B; BENECOAT BMI 40; BIO BLATT MEHLTAUMITTEL; BIOBLATT; CENTIOCAP 162US; CENTREX F; CENTROL 3F-UB; CENTROL 3FSB; CENTROLEX R; CENTROPHASE HR 2B; CENTROPHILL IP; CETINOL; E 322; E 322 (EMULSIFIER); EMULFLUID E; EMULMETIK 100; EMULSIFIER L; EMULTHIN M 35; GLIDDEX; GRANULESTIN; KELECIN; L 0023; LECI PS20P; LECI-PC 35P; LECIGRAN1000P; LECION; LECION P; LECIPRIME 1500; LECIPRIME1800IP; LECITHINE; LECITHINON; LECITHOL; LECIWET WD 120; LIPOID S 45; LIPOTIN100UB; LIPOTIN NE; METARIN P; PHOSPHOLIPIDS, LECITHIN COM. PREPNS.; PHOSPHOLIPON 85G; PHOSPHOLUTEIN; PLANTICIN; SICO-NS; SLP-PI POWDER; STERNPRIMEN 10 TOP; SUNLECITHIN L 6; TINODERM P; TOPCITIN 50; TROYKYD LECITHIN WD; ULTRALEC; VAMOTHIN SBX; YELKIN SS; YELKIN TS; and YELKIN TTS. The principal quality parameters for commercial lecithins are: phospholipid content (measured as percent acetone insolubles), free acidity, non-lipid impurities (measured as hexane insolubles), viscosity and color. Alternatively, the phospholipid containing drift reduction agent may be prepared without use of a commercially available lecithin-containing product. In some embodiments of the compositions disclosed herein, the phospholipid containing drift reduction agent includes liquid lecithins such as soybean based lecithins comprising mixtures of acetone insolubles, oils, and water. In some embodiments, the acetone insolubles may comprise 60% to 65% by weight, or about 62% by weight of the lecithin. The acetone insolubles in the lecithin may comprise carbohydrates and polar lipids such as phospholipids and glycolipids. In some embodiments, the phospholipids are selected from the group consisting of phosphatidylcholines, phosphatidylethanolamines, phosphatidylserines and phosphatidylinositols.

The phospholipid component of the drift reduction agent may be used in amounts of between about 10% and about 60% (weight:weight or volume:volume) of the drift reduction agent or of the combination water conditioning adjuvant and drift reduction agent. In some embodiments, the phospholipid component may be about 20%, about 22%, about 24%, about 26%, about 28%, about 30%, about 32%, about 34%, about 36%, about 38%, about 40%, about 42%, about 44%, about 46%, about 48%, about 50%, about 52%, about 54%, about 56%, about 58% or about 60% (weight:weight or volume:volume) of the drift reduction agent or of the combination composition comprising both water conditioning adjuvant and drift reduction agent. In some embodiments, the phospholipid component is less than or equal to 20%, is less than or equal to 22%, is less than or equal to 24%, is less than or equal to 26%, is less than or equal to 28%, is less than or equal to 30%, is less than or equal to 32%, is less than or equal to 34%, is less than or equal to 36%, is less than or equal to 38%, is less than or equal to 40%, is less than or equal to 42%, is less than or equal to 44%, is less than or equal to 46%, is less than or equal to 48%, or is less than or equal to 50%, less than or equal to 52%, less than or equal to 54%, less than or equal to 56%, less than or equal to 58%, or less than or equal to 60% (weight:weight or volume:volume) of the drift reduction agent or combination composition comprising both water conditioning adjuvant and drift reduction agent.

In some embodiments the optional oils of the drift reduction agent comprise 10-50% by weight, or 34% to 40% by weight, or 36% to 38% by weight, and in some embodiments water comprises about 5% or less by weight, and in some embodiments water comprises about 1% or less by weight of the combination composition comprising water conditioning adjuvant and drift reduction agent or of the drift reduction agent. In one embodiment the oil comprises methyl esters such as methyl soyate.

The oils can comprise neutral lipids such as triglycerides, including but not limited to soybean oil. In one embodiment, the oil is methylated seed oil (MSO). Other embodiments include other oils such as mineral oil, vegetable oil, ethylated seed oil, butylated seed oil, soybean oil, sunflower oil, cotton seed oil, crop oil concentrate and methylated soybean oil.

The oil component is optionally included in the drift reduction agents of the present invention to make the phospholipid mixture less viscous and easier to pump and stir during the spraying process. The drift reduction agent of the present invention optionally includes a non-ionic surfactant to allow the drift reduction agent to more easily dissolve into aqueous solutions and form aqueous spray compositions.

The drift reduction agent may also further comprise a surfactant. In addition to any other surfactants mentioned herein, the surfactant can comprise a non-ionic surfactant such as polyoxyethylene ether (an ethoxylated alcohol) of the formula $RO(CH_2CH_2O)_nH$, where R is a linear, primary alcohol and n is the number of ethylene oxide units. In some embodiments, the non-ionic surfactant is the polyoxyethylene ether, optionally TOMODOL 1-5, where R is a linear, C1-11 alkyl group and n=5 to make the formula $H_{23}C_{11}O(CH_2CH_2O)_5H$. Other surfactants such as alkyl polyoxyethylene ethers, polyoxypropylene glycol, alkyl phenol ethoxylates, alcohol ethoxylates, a sugar ether, glucoside alkyl ethers, sucrose esters, sorbitan ester ethoxylates, crop oil concentrates, morpholine amide and block copolymers can be used.

The water conditioning adjuvant of the invention may be mixed with the drift reduction agent to result in the combination composition for agricultural use in any proportions that will result in effective water conditioning and drift reduction. In some embodiments, the water conditioning adjuvant can comprise between about 25% and about 75% of the final composition, with the drift reduction agent comprising between about 75% and about 25%, respectively. It is noted that the adjuvant composition for agricultural use can then be further diluted with, e.g. carrier water, bioactive agents, and the like, in which case the proportion of each component, e.g. the water conditioning adjuvant and the drift reduction agent, will proportionally be reduced in the diluted composition for agricultural use.

The adjuvant compositions for agricultural use may further comprise (e.g., be mixed with) water and/or bioactive materials such as pesticides, herbicides, fungicides, insecticides, acaricides, nematocides, foliar nutrients, defoliants, plant growth regulators, and molluscicides.

The Water Quality Association of the United States defines hard water as having dissolved mineral hardness of 1 GPG (grain per gallon) or more. Definitions of hardness of water: Soft Water—less than 1 gpg; Slightly Hard—1-3.5 gpg; Moderately Hard—3.5-7 gpg; Very Hard—7-10 gpg; Extremely Hard—over 10 gpg. Carrier water for the spray solutions of the present invention may include any of these water hardness types as described above. The adjuvant compositions are especially suitable for use with hard water to minimize disadvantages arising from use of hard water. Water in the spray mixture may be of any ratio as is known in the art, in some instances may be between 0.25% and 5% by volume of combination composition for agricultural use.

The herbicides are optionally selected from the group consisting of glyphosate (N-phosphonomethylglycine), acifluorfen (5-(2-chloro-4-(trifluoromethyl)phenoxy)-2-nitrobenzoic acid), chloramben (3-amino-2,5-dichlorobenzoic acid), 2,4-D ((2,4-dichlorophenoxy)acetic acid), endothal (7-oxabicyclo(2.2.1)heptane-2,3-dicarboxylic acid), mecoprop (2-(2-methyl-4-chlorophenoxy)propionic acid), picloram (4-amino-3,5,6-trichloropyridine-2-carboxylic acid), 2,4,5-T((2,4,5-trichlorophenoxy)acetic acid), benzac (2,3,6-trichlorobenzoic acid), dicamba (3,6-dichloro-o-anisic acid), MCPA (4-chloro-o-tolyloxyacetic acid), dalapon (2,2-dichloropropionic acid), dichlorprop (2-(2,4-dichlorophenoxyl)propionic acid), MCPB (4-(4-chloro-o-tolyloxy)butyric acid), bialaphos (L-2-amino-4-((hydroxy)(methyl)phosphinoyl)butyryl-L-alanyl-L-alanine), glufosinate ((3-amino-3-carboxypropyl)methylphosphinate), imazethapyr (2-{4,5-dihydro-4-methyl-4-(1-methylethyl)-5-oxo-1H-imidazol-2-yl}-5-ethyl-3-pyridinecarboxylic acid), imazaquin (2-{4,5-dihydro-4-methyl-4-(1-methylethyl)-5-oxo-1H-imidazol-2-yl}-3-quino linecarboxylic acid), and mixtures thereof. In some embodiments the herbicide is an isopropylamine and/or potassium salt of glycophosate or other salts of glyphosate or glufosinate (e.g., ROUNDUP ULTRAMAX or ROUNDUP WEATHERMAX from Monsanto Company or other suppliers), and may be mixed in with the adjuvant suitable for agricultural use in any art-known and suitable amount, as directed by the manufacturer.

The compositions of the present invention also optionally include one or more compositions selected from the group consisting of buffering agents, defoaming agents, wetting agents, sticking agents, and tank cleaners.

EXAMPLES

The following examples are provided for illustrative purposes only and are not intended to limit the scope of the invention as defined by the appended claims. All examples described herein should be considered in the context of standard techniques, which are well known and routine to those of skill in the art.

Example 1. Lecithin Stability in AQ 216 Mixture Containing Sulfuric Acid and Tallow Amine Lecithin is known to be unstable in a sulfuric acid environment. As shown in Table 1, products containing lecithin, such as AIRLINK (UCPA LLC), LIBERATE (UAP) and LI700 (UAP) react differently with sulfuric acid, urea sulfate and with a mixture of sulfuric acid and tallow amine (AQ 216). For each reaction with urea sulfate and AQ 216, the urea sulfate was mixed thoroughly or AQ 216 was mixed thoroughly, before the addition of the lecithin composition. The results of Table 1 show that 50 mL of each of the referenced lecithin compositions reacted adversely with 3 mL of sulfuric acid, forming a precipitate; 50 mL of each of the lecithin compositions reacted adversely with urea sulfate comprising an equivalent amount of sulfuric acid, forming a gel; whereas 50 mL of each of the lecithin compositions did not react adversely with AQ 216 comprising an equivalent amount of sulfuric acid, maintaining a clear solution for 12 hours and longer (data not shown).

TABLE 1

Results of Lecithin Addition to Sulfuric Acid, Urea Sulfate and AQ 216

| Treatment | Ratio | Lecithin Composition | Notes | Time 1 hour | Time 12 Hours |
|---|---|---|---|---|---|
| Sulfuric Acid | 3 mL:50 mL | AIRLINK | Dark Precipitate | More precipitate | More precipitate |
| Urea Sulfate | 6 mL:50 mL | AIRLINK | Cloudy | Cloudy Separate | Gel with separate Liquid |
| AQ 216 | 6 mL:50 mL | AIRLINK | Clear | Clear | Clear |
| Sulfuric Acid | 3 mL:50 mL | LI 700 | Dark Precipitate | More precipitate | More precipitate |
| Urea Sulfate | 6 mL:50 mL | LI 700 | Cloudy | Cloudy Separate | Gel with separate Liquid |
| AQ 216 | 6 mL:50 mL | LI 700 | Clear | Clear | Clear |
| Sulfuric Acid | 3 mL:50 mL | LIBERATE | Dark Precipitate | More precipitate | More precipitate |
| Urea Sulfate | 6 mL:50 mL | LIBERATE | Cloudy | Cloudy Separate | Gel with separate Liquid |
| AQ 216 | 6 mL:50 mL | LIBERATE | Clear | Clear | Clear |

Sulfuric Acid: 95% Concentrated
Urea Sulfate: 45% Sulfuric (95% concentrated) + 40% Urea
AQ 216: 48% Sulfuric acid (95% concentrated) + 48% Tallow amine + 4% Diethylene glycol (DEG)

The addition of a pre-mix of sulfuric acid plus tallow amine plus DEG (AQ 216) to these lecithin containing products did not affect the products in a negative way. This is a surprising result as one of ordinary skill in the art would reasonably expect sulfuric acid to adversely react with lecithin resulting in undesirable by-products.

Example 2. Process for AQ 284 Synthesis

The process of making AQ 284 which is a combination water conditioning adjuvant and drift reduction composition requires separately preparing AQ 283 which is a water conditioning adjuvant and AQ 323 which is a drift reduction agent and then combining AQ 283 and AQ 323.

AQ 283 water conditioning adjuvant was prepared by adding the components of Table 2 in the order indicated. The components were added at room temperature and the composition was mixed to homogeneity after the addition of the component of each step. Table 2 provides for the preparation of a 100 lb batch of AQ 283. The final density of AQ 283 is 9.3679 lbs/gallon.

TABLE 2

AQ 283 Water Conditioning Adjuvant

| Step | Component | Weight Percent | Weight of Component Added (lbs) | Density of Component lbs/gallon | Volume of Component Added (gallons) |
|---|---|---|---|---|---|
| Step 1 | DEG | 25 | 25 | 9.35 | 2.67 |
| Step 2 | TC101 | 0 | 0 | 8.4 | 0.00 |
| Step 3 | TERWET | 45 | 45 | 8.5 | 5.29 |
| Step 4 | Sulfuric Acid | 12 | 12 | 15.35 | 0.78 |
| Step 5 | DEG | 18 | 18 | 9.35 | 1.93 |

The volume of components to be added was determined by dividing the weight of the component to be added by the density of said component. DEG, diethylene glycol, was added at two different steps first at Step 1 and then at Step 5. TC101 is an antifoaming agent added at approximately 0.001% by weight. TERWET is tallow amine blended with emulsifier, comprising approximately 78% tallow amine and approximately 22% emulsifier. The sulfuric acid used was concentrated 98% sulfuric acid which had a density just under 15.35 lbs/gallon. The sulfuric acid was added in the amount of 0.78 gallons/100 lb batch of AQ 283 as indicated in Table 2.

AQ 323 drift reduction agent was prepared by adding the components of Table 3 in the order indicated. The components were added at room temperature and the composition was mixed to homogeneity after the addition of the component of each step. Table 3 provides for the preparation of a 100 lb batch of AQ 323. The final density of AQ 323 is 8.0696 lbs/gallon.

TABLE 3

AQ323 Drift Reduction Agent

| Step | Component | Weight Percent | Weight of Component Added (lbs) | Density of Component lbs/gallon | Volume of Component Added (gallons) |
|---|---|---|---|---|---|
| Step 1 | AU810 | 40 | 40 | 7.5 | 5.33 |
| Step 2 | TERWET | 10 | 10 | 8.5 | 1.18 |
| Step 3 | SOLEC 3F-UB | 50 | 50 | 8.5 | 5.88 |

The volume of components to be added was determined by dividing the weight of the component to be added by the density of said component. AU810 is methylate seed oil. TERWET, as above, is tallow amine blended with emulsifier, comprising approximately 78% tallow amine and approximately 22% emulsifier. SOLEC 3F-UB is soy lecithin.

AQ 284 combination water conditioning adjuvant and drift reduction composition was prepared by combining 50% AQ 283 water conditioning adjuvant and 50% AQ 323 drift reduction agent. Table 4 provides for the preparation of a 100 lb batch of AQ 284. The final density of AQ 284 is 8.6715 lbs/gallon.

TABLE 4

AQ 284 Combination Water Conditioning Adjuvant and Drift Reduction Agent

| Step | Component | Weight Percent | Weight of Component Added (lbs) | Density of Component lbs/gallon | Volume of Component Added (gallons) |
|---|---|---|---|---|---|
| Step 1 | AQ 283 | 50 | 50 | 9.37 | 5.34 |
| Step 2 | AQ 323 | 50 | 50 | 8.07 | 6.20 |

Example 3. AQ 216 Water Conditioning Adjuvant

AQ 216 water conditioning adjuvant was prepared according to the general procedure as shown in Example 2 for AQ 283. AQ 216 contains 48% TERWET, 48% sulfuric acid (98% concentrated) and 2% DEG.

Example 4. AQ 236 Combination Water Conditioning Adjuvant and Drift Reduction Agent AQ 236 combination water conditioning adjuvant and drift reduction agent was prepared according to the general procedure as shown in Example 2. AQ 236 contains 38% TERWET; 4% sulfuric acid (98% concentrated); 32% DEG; 6.25% NP-9 (nonionic surfactant); 6.25% MSO and 12.5% lecithin.

Example 5. AQ 162 Combination Water Conditioning Adjuvant and Drift Reduction Agent AQ 162 combination water conditioning adjuvant and drift reduction agent was prepared according to the general procedure as shown in Example 2. AQ 162 contains 30% TERWET; 4% sulfuric acid (98% concentrated); 25% DEG; 20% MSO and 21% lecithin.

Example 6. AQ 163 Combination Water Conditioning Adjuvant and Drift Reduction Agent AQ 163 combination water conditioning adjuvant and drift reduction agent was prepared according to the general procedure as shown Example 2. AQ 163 contains 38% TERWET; 4% sulfuric acid (98% concentrated); 32% DEG; 12.5% MSO and 12.5% lecithin.

Example 7. AQ 268 Drift Reduction Agent

AQ 268 drift reduction agent was prepared by adding the components of Table 5 in the order indicated. The components were added at room temperature and the composition was mixed to homogeneity after the addition of the component of each step. Table 5 provides for the preparation of a 100 lb batch of AQ 268. The final density of AQ 268 is 8.2988 lbs/gallon.

TABLE 5

AQ 268 Drift Reduction Agent

| Step | Component | Weight Percent | Weight of Component Added (lbs) | Density of Component lbs/gallon | Volume of Component Added (gallons) |
|---|---|---|---|---|---|
| Step 1 | AU810 | 25 | 25 | 7.5 | 3.33 |
| Step 2 | TERWET | 15 | 15 | 8.5 | 1.76 |
| Step 3 | DEG | 10 | 10 | 9.35 | 1.07 |
| Step 4 | SOLEC 3F-UB | 50 | 50 | 8.5 | 5.88 |

The volume of components to be added was determined by dividing the weight of the component to be added by the density of said component. AU810 is methylate seed oil. TERWET, as above, is tallow amine blended with emulsifier, comprising approximately 78% tallow amine and approximately 22% emulsifier. SOLEC 3F-UB is soy lecithin.

Example 8. Glyphosate Efficacy Under Hard Water Conditions

AQ 162 showed excellent hard water conditioning, reduced the pH of the spray solution which is beneficial for glyphosate efficacy and showed excellent surfactant effects as shown in the data of FIG. 1 for the relative control of 4 indicator species by way of comparison to AIR LINK (commercial standard—drift reduction agent) and FULL LOAD (water conditioning adjuvant).

Example 9. Percent of Droplets Less than 210, 150 and 105 Microns

AQ 162 and AQ 163 were compared with AMS, AIR-LINK or INTERLOCK in combination with ROUNDUP, in droplets size and percentage of smaller droplets. AQ 162 showed equivalent reduction in terms of fine droplets (droplets less than 150 microns) compared to commercial standards (AIRLINK and INTERLOCK) as shown in FIG. 2.

Example 10. Evaluation of XR11002 Nozzle and Spray Solutions for Effects on Droplet Size Distribution Spray solutions were analyzed with a Sympatec Helos Vario KF particle size analyzer. With a R6 lens installed, it is capable of detecting particle sizes in a range from 0.5 to 1550 microns. This system uses laser diffraction to determine particle size distribution. The width of the nozzle plume was analyzed by moving the nozzle across the laser by means of a linear actuator. Five spray solutions were tested with a XR11002 nozzle at 40 psi. Results for droplet size are in Table 6.

The data of Table 6 show that AQ 284 provides equivalent increase in droplet size to the industry standard INTERLOCK at a 95% confidence level, reflected in the percent of droplets <150 microns belonging to statistical category "c" indicating that 33.14 and 32.87 are not statistically different at a 95% confidence level and the percent of droplets <105 microns belonging to statistical category "d" indicating that 15.46 and 15.71 are not statistically different at a 95% confidence level. While AQ 284 matches "industry standard" levels for increased droplet size, AQ 284 shows higher efficacy in field efficiency percent control of volunteer wheat.

In addition, the data of Table 6 show that AQ 284 reduced the percent of droplets under 150 microns in size, nearly 16% compared to RPM+AMS. AQ 284 provided equivalent increase in droplet size as AQ 268 (drift reduction alone) indicating that the combination of water conditioning adjuvant in AQ 284 did not reduce efficacy for increasing droplet size.

TABLE 6

Spray Solution Additive Effects on Droplet Size and Consistency

| Treatment | Pct < 105 μm | Pct < 150 μm | Pct > 730 μm | Relative Span | Field Efficacy % Control Vol. Wheat |
|---|---|---|---|---|---|
| 1. Water | 16.14 d | 31.88 c | 0.00 a | 1.30 cd | 0 |
| 2. RPM + AMS | 29.36 a | 48.78 a | 0.00 a | 1.60 a | 74 |
| 3. RPM + AMS + INTERLOCK + NIS | 15.46 d | 33.14 c | 0.04 a | 1.26 e | 92 |
| 4. RPM + AQ 284 | 15.71 d | 32.87 c | 0.00 a | 1.28 de | 96 |
| 5. RPM + AQ 268 + AMS + NIS | 15.40 d | 32.99 c | 0.11 a | 1.27 e | 97 |

Spray tip = XR 11002 at 40 psi;
RPM = ROUNDUP POWER MAX at 22 oz/acre; AMS—Ammonium Sulfate at 17 lb/100 gal; Nonionic Surfactant (NIS) = ACTIVATOR 90 at .25% v/v; AQ 284 or AQ 268 at .25% v/v;
values within the same statistical category letter label (a-e) do not have any statistical difference from other values within the same statistical category letter label, at a 95% confidence level

Example 11. Drift Reduction Testing of Combination Water Conditioning Adjuvant and Drift Reduction Composition A study using a large electric fan was conducted out of doors with the fan wind blowing perpendicular to the direction of the spray pattern. A $CO_2$ powered backpack sprayer equipped with XR 11002 spray tips delivering 20 gpa at 40 psi was used to make the different spray treatments with dicamba. Petri dishes were placed downwind at 0, 2, 5, and 8 feet from the spray pattern. The petri dishes were collected, rinsed, and the rinsate subjected to HPLC analysis to quantify the amount of herbicide collected.

Table 7 provides study data for the amount of dicamba collected from petri dishes up to 8 feet away from the spray boom. The amount collected with no drift reduction was the least, indicating that the fine droplets in the spray without a drift reduction agent dried and floated out of the collection zone. The estimated drift loss from the spray without a drift reduction agent was 13%. The AQ 284 combination water conditioning adjuvant and drift reduction composition reduced the loss from drift to less than 5%. In comparison to AQ 268 drift reduction agent alone, Table 7 shows that combining water conditioning adjuvant with drift reduction agent, as in AQ 284, resulted in minimal negative impact on drift reduction properties.

TABLE 7

Results of Drift Reduction Testing

| Treatment # | Treatment | Rate | Capture Distance Feet | Micrograms Collected | Theoretical Captured % |
|---|---|---|---|---|---|
| 1 | AMS | 17 lb/100 gal | 0 | 391 | 77.26 |
|  | Dicamba | 0.5 lb/a | 2 | 49 | 9.7 |
|  |  |  | 5 | 0 | 0 |
|  |  |  | 8 | 0 | 0 |
|  |  |  | Total | 440 | 86.96 |
| 2 | AMS | 17 lb/100 gal | 0 | 383.86 | 75.77 |
|  | Dicamba | 0.5 lb/a | 2 | 120.24 | 23.73 |
|  | NIS | 0.25% v/v | 5 | 2.71 | 0.53 |
|  | INTERLOCK | 4 oz/a | 8 | 0.29 | 0.05 |
|  |  |  | Total | 507.1 | 100.08 |
| 3 | AQ 284 | 0.25% v/v | 0 | 373.2 | 73.66 |
|  | Dicamba | 0.5 lb/a | 2 | 104.95 | 20.72 |
|  |  |  | 5 | 3.95 | 0.77 |
|  |  |  | 8 | 2.63 | 0.51 |
|  |  |  | Total | 484.73 | 95.66 |
| 4 | AQ 268 | 0.25% v/v | 0 | 396.07 | 78.18 |
|  | Dicamba | 0.5 lb/a | 2 | 84.28 | 16.34 |
|  |  |  | 5 | 6.83 | 1.35 |
|  |  |  | 8 | 1.28 | 0.25 |
|  |  |  | Total | 488.46 | 96.12 |

Example 12. Field Studies of Combination Water Conditioning Adjuvant and Drift Reduction Composition Two field studies were conducted to test the efficacy of the AQ 284 combination water conditioning adjuvant and drift reduction composition compared to the commercial standard (INTERLOCK). Studies consisted of 3 replications arranged in a randomized complete block design. The field studies were conducted in field plots that were 10×30 feet in size which were wheat fallow fields under a linear irrigation system where supplemental irrigation was used to promote excellent weed growth. The weeds in the test area were common lambsquarter, kochia and redroot pigweed. The order of increasing susceptibility of these weeds was common lambsquarter, kochia and redroot pigweed. The study was conducted with hard water conditioned with a Zn acetate micronutrient product, AWAKEN, to provide a hard water cation level of 2,000 ppm. Field applications were made with a $CO_2$ powered backpack sprayer with a 6 nozzle boom.

Table 8 shows the results of the field studies. AQ 284 at a rate of 0.5% v/v had the best efficacy of drift reduction candidates. The AQ 284 formulation demonstrated equivalent or better efficacy as seen with the commercial standard which is a combination of three components consisting of: ammonium sulfate 17 lb/100 gallons of spray solution+ 0.25% v/v nonionic surfactant+INTERLOCK 4 fluid ounces/acre.

TABLE 8

Field Studies for Weed Control

| Treatment # | Treatment Name | Rate | Avg. Weed % Control TEST 1 46 Days After Application | Avg. Weed % Control TEST 2 31 Days After Application |
|---|---|---|---|---|
| 1 | Untreated | | 0.0 | 0.0 |
| 2 | TOUCHDOWN HITEC | 0.70 lb/acre | 11.7 | 78.3 |
| 3 | TOUCHDOWN HITEC AMS | 0.70 lb/acre 17 lb/100 gal | 71.0 | 80.0 |
| 4 | TOUCHDOWN HITEC AMS INTERLOCK NIS | 0.70 lb/acre 17 lb/100 gal 4 fl oz/acre 0.25% v/v | 88.0 | 74.3 |
| 5 | TOUCHDOWN HITEC AQ 284 | 0.70 lb/acre 0.25% v/v | 80.7 | 96.3 |
| 6 | TOUCHDOWN HITEC AQ 284 | 0.70 lb/acre 0.50% v/v | 86.0 | 96.0 |
| 7 | TOUCHDOWN HITEC AQ 268 | 0.70 lb/acre 0.25% v/v | 82.7 | 97.3 |
| 8 | TOUCHDOWN HITEC FULL LOAD | 0.70 lb/acre 2 qt/acre | 86.7 | 97.0 |

Example 13. Greenhouse Study of Combination Water Conditioning Adjuvant and Drift Reduction Composition A greenhouse study was conducted to test the efficacy of the AQ 284 combination water conditioning adjuvant and drift reduction composition compared to the commercial standard (INTERLOCK). Greenhouse research was conducted with individual plants growing in 3×3×3 inch pots. Greenhouse treatments were applied with a track sprayer using an 8002 E single nozzle applying 20 gpa. When AQ 284 was added to glyphosate, it provided weed control, particularly at the 0.25% v/v rate, equivalent to the commercial standard: glyphosate+INTERLOCK+ammonium sulfate+nonionic surfactant.

Example 14. Drift Reduction Agents Comprising Emulsifier

Glyphosate Solutions were analyzed with a Sympatec Helos/Vario KR particle size analyzer. With the R7 lens installed, it is capable of detecting particle sizes in a range from 18 to 3500 microns. This system uses laser diffraction to determine particle size distribution. The width of the nozzle plume was analyzed by moving the nozzle across the laser by means of a linear actuator. All testing was performed in a low speed wind tunnel at 15 mph. Spray solutions were evaluated through several nozzles, and each treatment was replicated at least three times. The nozzle tested was the XR11002 at 40 psi. Results are in the table that follows. The percent less than 105 μm (Pct<105 μm) is

TABLE 9

Greenhouse Studies for Weed Control

| Trt No. | Treatment Name | Rate | Corn % Control 18 Days After Application | Sunflower % Control 18 Days After Application | Wheat % Control 18 Days After Application | Average % Control 18 Days After Application |
|---|---|---|---|---|---|---|
| 1 | Untreated | | 0.0 | 0.0 | 0.0 | 0.0 |
| 2 | Glyphosate | 0.375 lb/acre | 10.0 | 15.0 | 15.0 | 13.3 |
| 3 | Glyphosate AMS | 0.375 lb/acre 17 lb/100 gal | 65.0 | 70.0 | 50.0 | 61.7 |
| 4 | Glyphosate AMS NIS INTERLOCK | 0.375 lb/acre 17 lb/100 gal 0.25% v/v 4 fl oz/acre | 60.0 | 75.0 | 40.0 | 58.3 |
| 5 | Glyphosate AQ 284 | 0.375 lb/acre 0.25% v/v | 60.0 | 65.0 | 40.0 | 55.0 |
| 6 | Glyphosate AQ 284 | 0.375 lb/acre 0.50% v/v | 55.0 | 60.0 | 35.0 | 50.0 |
| 7 | Glyphosate AQ 268 | 0.375 lb/acre 0.25% v/v | 50.0 | 65.0 | 45.0 | 53.3 | the percentage of the spray volume that is 105 µm and smaller, with percent less than 141 µm (Pct<141 µm), 150 µm (Pct<150 µm), 210 µm (Pct<210 µm), and 730 µm (Pct<730 µm) being similar measurements. The data were analyzed using a mixed model ANOVA (PROC MIXED) with Replication set as random in SAS 9.2. The mean separation were conducted at the α=0.05 level using a Tukey adjustment.

In the data of Table 10, the smaller the number in the column for any particular droplet size range (the fewer small droplets), the better the drift reduction effect as larger droplets travel less distance. Data is provided for INTERLOCK which is the industrial leader for drift control. Glyphosate alone (rows labeled NIS+AMS) serves as the control in the absence of drift reduction. A comparison of the

TABLE 10

Droplet Size by Micron.

| Additive | % <105 µm | LSD | % <141 µm | LSD | % <150 µm | LSD | % <210 µm | LSD | % <730 µm | LSD | Relative Span | LSD |
|---|---|---|---|---|---|---|---|---|---|---|---|---|
| NIS + AMS | 18.48 | a | 32.25 | a | 35.73 | a | 57.95 | ab | 100 | a | 1.42 | a |
| AQ785 | 9.51 | f | 21.86 | f | 25.22 | f | 49.82 | e | 100 | a | 1.17 | g |
| AQ790 | 10.06 | f | 23.15 | f | 26.67 | f | 51.97 | de | 100 | a | 1.18 | g |
| AQ843 | 16.2 | b | 30.48 | abc | 34.13 | abc | 57.09 | ab | 100 | a | 1.35 | bc |
| AQ844 | 16.41 | b | 30.99 | ab | 34.71 | ab | 57.99 | a | 100 | a | 1.37 | b |
| AQ796 | 14.5 | d | 28.59 | cd | 32.25 | cd | 56.18 | abc | 100 | a | 1.29 | de |
| Interlock ® | 12.13 | e | 25.51 | e | 29.05 | e | 52.91 | de | 100 | a | 1.24 | f |

In Table 10, NIS stands for non-ionic surfactant, AMS stands for ammonium sulfate, LSD stands for Least Significant Difference and Relative Span indicates the variation in droplet size. The greater the relative span number the more variation in droplet size. The codes in the LSD column indicate an LSD of 0.05. Treatments followed by the same letter are statistically similar and letters farther alphabetically apart indicate a statistically greater difference (e.g. a number where LSD is "a" is more different from a number the LSD of which is "f" than from a number the LSD of which is "b".

TABLE 11

Components of Additives

| Additives | Components of Additives | 4% $H_2SO_4$ | 8% AMADS | AQ763 |
|---|---|---|---|---|
| NIS + AMS | | | | |
| AQ785 | Sulfonate Emulsifier 15% + Fatty Acid 40% + MSO 30% + NIS Emulsifier 15% | Not Stable | Not Stable | Stable |
| AQ790 | Sulfonate Emulsifier 6% + Fatty Acid 16% + MSO 30% + NIS Emulsifier 6% + Lecithin 36% Amine Emulsifier 6% | Not Stable | Not Stable | Stable |
| AQ843 | Sulfonate Emulsifier 25% + Fatty Acid 40% + MSO 20% + NIS Emulsifier 15% | Not Stable | Not Stable | Stable |
| AQ844 | Lecithin 40% + Fatty Acid 30% + MSO 15% + NIS Emulsifier 15% | Not Stable | Not Stable | Stable |
| AQ796 | AQ763 30% + TOMADOL 600 30% + AQ790 40% | | | |
| INTERLOCK | | Not Stable | Not Stable | Stable |

In Table 11, NIS stands for non-ionic surfactant; AMS stands for ammonium sulfate; the sulfonate emulsifier is calcium dodecylbenzene sulfonate; the fatty acid consists mostly of myristic, palmitic, stearic, oleic, linoleic and linolenic fatty acids; MSO stands for methylated seed oil; NIS emulsifier means emulsion forming non-ionic surfactant; amine emulsifier means emulsion forming amine surfactant; TOMADOL 600 is ethoxylated linear alcohol surfactant; AMADS is monocarbamide dihydrogen sulfate solution.

data of Table 10 shows that AQ 785 and AQ 790 were more effective drift control agents than INTERLOCK.

In the data of Table 11, it is apparent that the listed drift reduction agents are not stable in 4% $H_2SO_4$ and not stable in 8% AMADS, but are stable in AQ763.

What is claimed is:

1. A composition for agricultural use, comprising:
   a water conditioning adjuvant comprising an amine surfactant and a concentrated mineral acid selected from the group consisting of sulfuric acid, perchloric acid, hydroiodic acid, hydrobromic acid, hydrochloric acid, nitric acid, and mixtures thereof; diethylene glycol; and
   a drift reduction agent selected from the group consisting of at least one phospholipid, vegetable colloids, non-derivatized guar gum, non-cationic derivatized guar gum, cationic guar gum, polyethylene oxides, poly (vinyl pyrrolidones), polyacrylamides, a non-ionic emulsifier, a cationic emulsifier which is not an amine surfactant, an anionic emulsifier, and mixtures thereof.

2. The composition of claim 1, wherein said drift reduction agent is at least one phospholipid.

3. The composition of claim 2, wherein said at least one phospholipid is selected from the group consisting of lecithin, phosphatidic acid, phosphotidyl ethanolamine, phosphatidylcholine, phosphatidylserine, phosphatidylinositol, phosphatidylinositol phosphate, phosphatidylinositol biphosphate, phosphatidylinositol triphosphate, and mixtures thereof.

4. The composition of claim 3, wherein said at least one phospholipid is lecithin.

5. The composition of claim 1, wherein said concentrated mineral acid is sulfuric acid.

6. The composition of claim 5, wherein said concentrated sulfuric acid is selected from the group consisting of 93% to 98% concentrated sulfuric acid.

7. The composition of claim 5, wherein said amine surfactant is selected from the group consisting of octyl amine, lauryl amine, stearyl amine, oleyl amine, tallow amine, cetylamine, N-tetradecyl amine, cocoamine, hydrogenated tallow amine, di(hydrogenated) tallow amine, dicoalkyl amine, N-tridecyltridecanamine, N-methylstearylamine, distearyl amine, ether amine, dialkyl ($C_8$-$C_{20}$) amine, and mixtures thereof.

8. The composition of claim 7, wherein said amine surfactant is tallow amine.

9. The composition of claim 8, wherein the concentration of tallow amine is equal to or greater than the concentration of sulfuric acid in the composition.

10. The composition of claim 9, wherein said composition further comprises an oil selected from the group consisting of free fatty acid, mineral oil, vegetable oil, methylated seed oil, ethylated seed oil, butylated seed oil, and mixtures thereof.

11. The composition of claim 9, wherein said composition further comprises an oil selected from soybean oil, sunflower oil, cotton seed oil, crop oil concentrate, methylated soybean oil, and mixtures thereof.

12. The composition of claim 10, wherein said oil is methylated seed oil.

13. The composition of claim 1, wherein said composition further comprises a non-ionic surfactant selected from the group consisting of an alkyl polyoxyethylene ether, polyoxypropylene glycol, an alkyl phenol ethoxylate, an alcohol ethoxylate, a sugar ether, a sucrose ester, a sorbitan ester ethoxylate, a crop oil concentrate, morpholine amide, a block copolymer, and mixtures thereof.

14. The composition of claim 1, wherein said composition does not contain and is not contacted with ammonium sulfate (AMS).

15. The composition of claim 14, wherein said composition comprises an emulsifier.

16. The composition of claim 15, wherein said composition comprises an additive selected from a buffering agent, a defoaming agent, a wetting agent, a sticking agent, a tank cleaner, and mixtures thereof.

17. The composition of claim 15, wherein the water content of the composition is below 5% (v/v), before dilution of the composition in carrier water.

18. The composition of claim 17, wherein the water content of the composition is below 1% (v/v), before dilution of the composition in carrier water.

19. The composition of claim 1, wherein said composition comprises 1-25% by weight or volume concentrated mineral acid, 10-50% by weight or volume amine surfactant, 10-60% by weight or volume phospholipid, 10-50% by weight or volume oil and 5-50% by weight or volume diethylene glycol.

20. The composition of claim 19, wherein said composition comprises 1-25% by weight or volume concentrated sulfuric acid, 10-50% by weight or volume tallow amine, 10-60% by weight or volume lecithin, 10-50% by weight or volume methylated seed oil and 5-50% by weight or volume diethylene glycol.

21. A process of preparing a composition for agricultural use comprising:
a) adding a concentrated mineral acid selected from the group consisting of sulfuric acid, perchloric acid, hydroiodic acid, hydrobromic acid, hydrochloric acid, nitric acid, and mixtures thereof to an amine surfactant to obtain a water conditioning adjuvant; and
b) adding the water conditioning adjuvant to diethylene glycol and a drift reduction agent selected from the group consisting of at least one phospholipid, vegetable colloids, non-derivatized guar gum, non-cationic derivatized guar gum, cationic guar gum, polyethylene oxides, poly (vinyl pyrrolidones), polyacrylamides, a non-ionic emulsifier, a cationic emulsifier which is not an amine surfactant, an anionic emulsifier, and mixtures thereof.

22. The process of claim 21, wherein said drift reduction agent is at least one phospholipid.

23. The process of claim 22, wherein said at least one phospholipid is selected from the group consisting of lecithin, phosphatidic acid, phosphotidyl ethanolamine, phosphatidylcholine, phosphatidylserine, phosphatidylinositol, phosphatidylinositol phosphate, phosphatidylinositol biphosphate, and phosphatidylinositol triphosphate, and mixtures thereof.

24. The process of claim 23, wherein said at least one phospholipid is lecithin.

25. The process of claim 21, wherein said concentrated mineral acid is sulfuric acid.

26. The process of claim 25, wherein said concentrated sulfuric acid is selected from the group consisting of 93% to 98% concentrated sulfuric acid.

27. The process of claim 25, wherein said amine surfactant is selected from the group consisting of octyl amine, lauryl amine, stearyl amine, oleyl amine, tallow amine, cetylamine, N-tetradecyl amine, cocoamine, hydrogenated tallow amine, di(hydrogenated) tallow amine, dicocoalkyl amine, N-tridecyltridecanamine, N-methylstearylamine, distearyl amine, ether amine, dialkyl (C8-C20) amine, and mixtures thereof.

28. The process of claim 27, wherein said amine surfactant is tallow amine.

29. The process of claim 28, wherein the concentration of tallow amine is equal to or greater than the concentration of sulfuric acid in the composition.

30. The process of claim 29, wherein the process further comprises adding an oil selected from the group consisting of free fatty acid, mineral oil, vegetable oil, methylated seed oil, ethylated seed oil, butylated seed oil, and mixtures thereof.

31. The process of claim 29, wherein the process further comprises adding an oil selected from soybean oil, sunflower oil, cotton seed oil, crop oil concentrate, methylated soybean oil, and mixtures thereof.

32. The process of claim 30, wherein said oil is methylated seed oil.

33. The process of claim 21, wherein said process further comprises adding a non-ionic surfactant selected from the group consisting of an alkyl polyoxyethylene ether, polyoxypropylene glycol, an alkyl phenol ethoxylate, an alcohol ethoxylate, a sugar ether, a sucrose ester, a sorbitan ester ethoxylate, a crop oil concentrate, morpholine amide, a block copolymer, and mixtures thereof.

34. The process of claim 21, wherein said composition does not contain and is not contacted with ammonium sulfate (AMS).

35. The process of claim 34, wherein said process further comprises adding an emulsifier.

36. The process of claim 35, wherein said process further comprises adding an additive selected from a buffering agent, a defoaming agent, a wetting agent, a sticking agent, a tank cleaner, and mixtures thereof.

37. The process of claim 35, wherein the water content of the composition is maintained below 5% (v/v), before dilution of the composition in carrier water.

38. The process of claim 37, wherein the water content of the composition is maintained below 1% (v/v), before dilution of the composition in carrier water.

39. A composition prepared by a process comprising:
a) adding a concentrated mineral acid selected from the group consisting of sulfuric acid, perchloric acid, hydroiodic acid, hydrobromic acid, hydrochloric acid, nitric acid, and mixtures thereof to an amine surfactant to obtain a water conditioning adjuvant; and b) adding the water conditioning adjuvant to diethylene glycol and a drift reduction agent selected from the group consisting of at least one phospholipid, vegetable colloids, non-derivatized guar gum, non-cationic derivatized guar gum, cationic guar gum, polyethylene oxides, poly (vinyl pyrrolidones), polyacrylamides, a non-ionic emulsifier, a cationic emulsifier which is not an amine surfactant, an anionic emulsifier, and mixtures thereof.

40. The composition of claim 39, wherein said drift reduction agent is at least one phospholipid.

41. The composition of claim 40, wherein said at least one phospholipid is selected from the group consisting of lecithin, phosphatidic acid, phosphotidyl ethanolamine, phosphatidylcholine, phosphatidylserine, phosphatidylinositol, phosphatidylinositol phosphate, phosphatidylinositol biphosphate, and phosphatidylinositol triphosphate, and mixtures thereof.

42. The composition of claim 41, wherein said at least one phospholipid is lecithin.

43. The composition of claim 39, wherein said concentrated mineral acid is sulfuric acid.

44. The composition of claim 43, wherein said concentrated sulfuric acid is selected from the group consisting of 93% to 98% concentrated sulfuric acid.

45. The composition of claim 43, wherein said amine surfactant is selected from the group consisting of octyl amine, lauryl amine, stearyl amine, oleyl amine, tallow amine, cetylamine, N-tetradecyl amine, cocoamine, hydrogenated tallow amine, di(hydrogenated) tallow amine, dicocoalkyl amine, N-tridecyltridecanamine, N-methylstearylamine, distearyl amine, ether amine, dialkyl (C8-C20) amine, and mixtures thereof.

46. The composition of claim 45, wherein said amine surfactant is tallow amine.

47. The composition of claim 46, wherein the concentration of tallow amine is equal to or greater than the concentration of sulfuric acid in the composition.

48. The composition of claim 47, wherein the process further comprises adding an oil selected from the group consisting of free fatty acid, mineral oil, vegetable oil, methylated seed oil, ethylated seed oil, butylated seed oil, and mixtures thereof.

49. The composition of claim 47, wherein the process further comprises adding an oil selected from soybean oil, sunflower oil, cotton seed oil, crop oil concentrate, methylated soybean oil, and mixtures thereof.

50. The composition of claim 48, wherein said oil is methylated seed oil.

51. The composition of claim 39, wherein said process further comprises adding a non-ionic surfactant selected from the group consisting of an alkyl polyoxyethylene ether, polyoxypropylene glycol, an alkyl phenol ethoxylate, an alcohol ethoxylate, a sugar ether, a sucrose ester, a sorbitan ester ethoxylate, a crop oil concentrate, morpholine amide, a block copolymer, and mixtures thereof.

52. The composition of claim 39, wherein said process does not add to the composition and does not contact the composition with ammonium sulfate (AMS).

53. The composition of claim 52, wherein said process further comprises adding an emulsifier.

54. The composition of claim 53, wherein said process further comprises adding an additive selected from a buffering agent, a defoaming agent, a wetting agent, a sticking agent, a tank cleaner, and mixtures thereof.

55. The composition of claim 53, wherein said process further comprises maintaining the water content of the composition below 5% (v/v), before dilution of the composition in carrier water.

56. The composition of claim 55, wherein said process further comprises maintaining the water content of the composition below 1% (v/v), before dilution of the composition in carrier water.

57. A method for reducing drift during release of an aqueous composition suitable for treating agricultural acreage comprising the steps of:

a) forming the aqueous composition suitable for treating agricultural acreage by mixing the composition for agricultural use of claim 1, carrier water and a bioactive material; and b) spraying the aqueous composition on agricultural acreage;

wherein the composition is about 0.25% (v/v) to about 5% (v/v) of the aqueous composition.

58. The method of claim 57, wherein the bioactive material is selected from the group consisting of pesticides, herbicides, fungicides, insecticides, acaricides, nematocides, foliar nutrients, defoliants, plant growth regulators, molluscicides, and mixtures thereof.

59. The method of claim 58, wherein the bioactive material is selected from the group consisting of glyphosate (N-(phosphonomethyl)glycine), dicamba, and mixtures thereof.

60. The composition of claim 1, wherein the non-ionic emulsifier is selected from the group consisting of alcohols, alcohol ethoxylates, polyoxyethylene-polyoxypropylene-alkyl ethers, amine alkoxylates, fatty alcohol polyglycol ethers, fatty amine polyglycol ethers, fatty acid ethoxylates, fatty acid polyglycol esters, glyceride monoalkoxylates, alkanolamides, fatty acid alkanolamides, ethoxylated alkanolamides, ethoxylated esters, fatty acid alkylolamido ethoxylates, ethylene oxide-propylene oxide block copolymers, alkylphenol ethoxylates, alkyl glucosides, partial esters of aliphatic carboxylic acids with polyfunctional alcohols, polyethoxylated polystyrene phenyl ethers, amides of aliphatic carboxylic acids with alkanolamines, ethoxylated amides of aliphatic carboxylic acids with alkanolamines, morpholine amide, polyalkoxylated organopolysiloxanes, and mixtures thereof.

61. The composition of claim 1, wherein the cationic emulsifier is selected from the group consisting of primary, secondary and tertiary amines and salts thereof, alkyltrimethylammonium salts, dialkyldimethylammonium salts, trialkylmethylammonium salts, tetraalkylammonium salts, alkoxylated alkylammonium salts, ester quats, diamidoamine quats, alkyloxyalkyl quats, quaternary alkylphosphonium salts, tertiary alkylsulfonium salts, alkylimidazolium salts, alkyloxazolinium salts, alkylpyridium salts and N,N-dialkylmorpholinium salts; the cationic emulsifier may comprise chloride, bromide, methyl sulfate, sulfate or the like as counterion, and mixtures thereof.

62. The composition of claim 1, wherein the anionic emulsifier is selected from the group consisting of alkyl sulfates, arylsulfonates, fatty alcohol sulfates, alkylsulfonates, paraffinsulfonates, alkyl ether sulfates, alkyl polyglycol ether sulfates, fatty alcohol ether sulfates, alkylbenzenesulfonates, alkylnaphthylsulfonates, alkylphenyl ether sulfates, alkyl phosphates, phosphoric acid mono-, di-, and tri-esters, alkyl ether phosphates, ethoxylated fatty alcohol phosphoric esters, alkylphenyl ether phosphates, phosphonic esters, sulfosuccinic diesters, sulfosuccinic monoesters, ethoxylated sulfosuccinic monoesters, ulfosuccinamides, a olefinsulfonates, alkyl carboxylates, alkyl ether carboxylates, alkyl polyglycol carboxylates, fatty acid isethionate, fatty acid methyltauride, fatty acid sarcoside, arylsulfonates, naphthalenesulfonates, alkyl glyceryl ether sulfonates, sulfated oils, polyacrylates, a-sulfa fatty acid esters, and mixtures thereof.

63. The composition of claim 10, wherein the free fatty acid is selected from the group consisting of free C12-C18 saturated, unsaturated fatty acid, and mixtures thereof.

64. The composition of claim 13, wherein the sugar ether is selected from the group consisting of glucoside alkyl ether, xylose alkyl ether, arabinose alkyl ether, mannose alkyl ether, ribose alkyl ether, rhamnose alkyl ether, galactose alkyl ether, sucrose alkyl ether, maltose alkyl ether, lactose alkyl ether, fructose alkyl ether, raffinose alkyl ether, and mixtures thereof.

65. The process of claim 21, wherein the non-ionic emulsifier is selected from the group consisting of alcohols, alcohol ethoxylates, polyoxyethylene-polyoxypropylene-alkyl ethers, amine alkoxylates, fatty alcohol polyglycol ethers, fatty amine polyglycol ethers, fatty acid ethoxylates, fatty acid polyglycol esters, glyceride monoalkoxylates, alkanolamides, fatty acid alkanolamides, ethoxylated alkanolamides, ethoxylated esters, fatty acid alkylolamido ethoxylates, ethylene oxide-propylene oxide block copolymers, alkylphenol ethoxylates, alkyl glucosides, partial esters of aliphatic carboxylic acids with polyfunctional alcohols, polyethoxylated polystyrene phenyl ethers, amides of aliphatic carboxylic acids with alkanolamines, ethoxylated amides of aliphatic carboxylic acids with alkanolamines, morpholine amide, polyalkoxylated organopolysiloxanes, and mixtures thereof.

66. The process of claim 21, wherein the cationic emulsifier is selected from the group consisting of primary, secondary and tertiary amines and salts thereof, alkyltrimethylammonium salts, dialkyldimethylammonium salts, trialkylmethylammonium salts, tetraalkylammonium salts, alkoxylated alkylammonium salts, ester quats, diamidoamine quats, alkyloxyalkyl quats, quaternary alkylphosphonium salts, tertiary alkylsulfonium salts, alkylimidazolium salts, alkyloxazolinium salts, alkylpyridium salts and N,N-dialkylmorpholinium salts; the cationic emulsifier may comprise chloride, bromide, methyl sulfate, sulfate or the like as counterion, and mixtures thereof.

67. The process of claim 21, wherein the anionic emulsifier is selected from the group consisting of alkyl sulfates, arylsulfonates, fatty alcohol sulfates, alkylsulfonates, paraffinsulfonates, alkyl ether sulfates, alkyl polyglycol ether sulfates, fatty alcohol ether sulfates, alkylbenzenesulfonates, alkylnaphthylsulfonates, alkylphenyl ether sulfates, alkyl phosphates, phosphoric acid mono-, di-, and tri-esters, alkyl ether phosphates, ethoxylated fatty alcohol phosphoric esters, alkylphenyl ether phosphates, phosphonic esters, sulfosuccinic diesters, sulfosuccinic monoesters, ethoxylated sulfosuccinic monoesters, ulfosuccinamides, a olefinsulfonates, alkyl carboxylates, alkyl ether carboxylates, alkyl polyglycol carboxylates, fatty acid isethionate, fatty acid methyltauride, fatty acid sarcoside, arylsulfonates, naphthalenesulfonates, alkyl glyceryl ether sulfonates, sulfated oils, polyacrylates and/or a-sulfa fatty acid esters, and mixtures thereof.

68. The process of claim 30, wherein the free fatty acid is selected from the group consisting of free C12-C18 saturated and unsaturated fatty acid.

69. The process of claim 33, wherein the sugar ether is selected from the group consisting of glucoside alkyl ether, xylose alkyl ether, arabinose alkyl ether, mannose alkyl ether, ribose alkyl ether, rhamnose alkyl ether, galactose alkyl ether, sucrose alkyl ether, maltose alkyl ether, lactose alkyl ether, fructose alkyl ether, raffinose alkyl ether, and mixtures thereof.

70. The composition of claim 39, wherein the non-ionic emulsifier is selected from the group consisting of alcohols, alcohol ethoxylates, polyoxyethylene-polyoxypropylene-alkyl ethers, amine alkoxylates, fatty alcohol polyglycol ethers, fatty amine polyglycol ethers, fatty acid ethoxylates, fatty acid polyglycol esters, glyceride monoalkoxylates, alkanolamides, fatty acid alkanolamides, ethoxylated alkanolamides, ethoxylated esters, fatty acid alkylolamido ethoxylates, ethylene oxide-propylene oxide block copolymers, alkylphenol ethoxylates, alkyl glucosides, partial esters of aliphatic carboxylic acids with polyfunctional alcohols, polyethoxylated polystyrene phenyl ethers, amides of aliphatic carboxylic acids with alkanolamines, ethoxylated amides of aliphatic carboxylic acids with alkanolamines, morpholine amide, polyalkoxylated organopolysiloxanes, and mixtures thereof.

71. The composition of claim 39, wherein the cationic emulsifier is selected from the group consisting of primary, secondary and tertiary amines and salts thereof, alkyltrimethylammonium salts, dialkyldimethylammonium salts, trialkylmethylammonium salts, tetraalkylammonium salts, alkoxylated alkylammonium salts, ester quats, diamidoamine quats, alkyloxyalkyl quats, quaternary alkylphosphonium salts, tertiary alkylsulfonium salts, alkylimidazolium salts, alkyloxazolinium salts, alkylpyridium salts and N,N-dialkylmorpholinium salts; the cationic emulsifier may comprise chloride, bromide, methyl sulfate, sulfate or the like as counterion, and mixtures thereof.

72. The composition of claim 39, wherein the anionic emulsifier is selected from the group consisting of alkyl sulfates, arylsulfonates, fatty alcohol sulfates, alkylsulfonates, paraffinsulfonates, alkyl ether sulfates, alkyl polyglycol ether sulfates, fatty alcohol ether sulfates, alkylbenzenesulfonates, alkylnaphthylsulfonates, alkylphenyl ether sulfates, alkyl phosphates, phosphoric acid mono-, di-, and tri-esters, alkyl ether phosphates, ethoxylated fatty alcohol phosphoric esters, alkylphenyl ether phosphates, phosphonic esters, sulfosuccinic diesters, sulfosuccinic monoesters, ethoxylated sulfosuccinic monoesters, ulfosuccinamides, a olefinsulfonates, alkyl carboxylates, alkyl ether carboxylates, alkyl polyglycol carboxylates, fatty acid isethionate, fatty acid methyltauride, fatty acid sarcoside, arylsulfonates, naphthalenesulfonates, alkyl glyceryl ether sulfonates, sulfated oils, polyacrylates, a-sulfa fatty acid esters, and mixtures thereof.

73. The composition of claim 48, wherein the free fatty acid is selected from the group consisting of free C12-C18 saturated, unsaturated fatty acid, and mixtures thereof.

74. The composition of claim 51, wherein the sugar ether is selected from the group consisting of glucoside alkyl ether, xylose alkyl ether, arabinose alkyl ether, mannose alkyl ether, ribose alkyl ether, rhamnose alkyl ether, galactose alkyl ether, sucrose alkyl ether, maltose alkyl ether, lactose alkyl ether, fructose alkyl ether, raffinose alkyl ether, and mixtures thereof.

* * * * *